United States Patent [19]
Page et al.

[11] Patent Number: 5,466,020
[45] Date of Patent: Nov. 14, 1995

[54] BAYONET CONNECTOR FOR SURGICAL HANDPIECE

[75] Inventors: Jon P. Page, Broomfield; Robert B. Stoddard, Louisville, both of Colo.

[73] Assignee: Valleylab Inc., Boulder, Colo.

[21] Appl. No.: 367,420

[22] Filed: Dec. 30, 1994

[51] Int. Cl.⁶ ................................................ F16L 19/00
[52] U.S. Cl. .......................... 285/361; 285/376; 285/906; 215/332; 604/198
[58] Field of Search .................................. 285/361, 376, 285/397, 402, 401, 358, 307, 314, 360, 906; 604/905, 206; 220/295, 300, 301; 215/331, 332

[56] References Cited

U.S. PATENT DOCUMENTS

| | | | |
|---|---|---|---|
| 784,513 | 3/1905 | Brockelbank | 215/332 |
| 3,076,904 | 2/1963 | Kleesattel et al. | |
| 3,927,783 | 12/1975 | Bogert | 215/332 |
| 4,306,734 | 12/1981 | Hinshaw et al. | 285/402 |
| 4,482,073 | 11/1984 | Gagliardi | 215/332 |
| 4,494,555 | 1/1985 | Abrioux et al. | |
| 4,708,370 | 11/1987 | Todd | 285/396 |
| 4,737,148 | 4/1988 | Blake | |
| 4,840,185 | 6/1989 | Hernandez | 604/198 |
| 4,932,940 | 6/1990 | Walker et al. | 604/198 |
| 4,943,282 | 7/1990 | Page et al. | 604/198 |

FOREIGN PATENT DOCUMENTS

| | | | |
|---|---|---|---|
| 245794 | 3/1963 | Australia | 220/295 |
| 651256 | 3/1928 | France | 215/332 |
| 2461271 | 12/1974 | Germany. | |
| 632147 | 9/1982 | Switzerland. | |

Primary Examiner—Dave W. Arola
Assistant Examiner—Heather Chun Shackelford
Attorney, Agent, or Firm—Peter C. Richardson; Lawrence C. Akers; Aaron Passman

[57] ABSTRACT

A connection of first and second members wherein each has a body and a connecting end with an inner surface so the second connecting end has an outer surface shaped for telescoping into the inner surface of the first connecting end. A shoulder is located on the second member and a groove is in the outer surface of the second connecting end. A raised nub on the inner surface of the first connecting end is radially inward to engage the groove. An elastomeric gasket is positioned to bear against the shoulder and be compressed between the first and second bodies. An engaging trough in the groove holds the first connecting end against the shoulder with the nub against the groove by the compression force of the gasket. An indexing trough in the groove positioned along the groove beyond the engaging trough allows the nub to follow therethrough and slightly compress the gasket thus giving the user a tactile indication that it has been rotated beyond the engaging trough. A method for fluid tight attachment of members of a medical device has steps including providing the connection of the first and second members with ends by telescoping the ends. Locating a groove for operating the groove as a cam and locating a raised nub of material on the inner surface of the first connecting end for positioning the raised nub to engage the groove for operating the raised nub as a follower of the cam are steps. Compressing a gasket seal between the first connecting end and the shoulder while making the gasket seal from an elastomeric material is a step. Positioning an engaging trough in the groove to hold the first and second connecting ends against each other is a step. Positioning an indexing trough in the groove so when the nub is rotatably forced past the engaging trough it will further compress the first end against the gasket is a step.

16 Claims, 3 Drawing Sheets

BAYONET CONNECTOR FOR SURGICAL HANDPIECE

FIELD OF THE INVENTION

This invention relates to an improved connector for attaching two members of a medical instrument to form a passage, where the members are substantially sealed to prevent fluid leakage in the attachment. More particularly, the connector provides tactile feedback to confirm proper seating of the members, and an indexing feature to prevent overtorquing the connection.

BACKGROUND OF THE DISCLOSURE

Certain medical devices must be disassembled after each surgical procedure for purposes of inspection, cleaning and sterilization. For example, the handpiece of an ultrasonic aspirator must be disassembled and handled according to certain procedures in order to assure that it will be safe and sterile for the next surgical procedure. Often these surgical devices are expensive to replace. Therefore it is desirable to have simplified assembly and disassembly procedures in order to avoid damage due to mishandling. Also, a simplified assembly procedure will help assure that the equipment will be properly prepared for use in the operating room.

Repeated assembly and disassembly of a connector in a medical device will expose the connector to stress from possible overtorquing, particularly where threaded connections or the equivalent are used. The danger in exposing a medical device to high stress is that cracks may develop, which if not detected could pose a risk, e.g. malfunctioning equipment. This is particularly a problem where the connection must be fluid tight, as even small cracks may allow fluid to seep and pose a risk of injury to a patient.

Special tools can be used to prevent overtorquing, such as calibrated torque wrenches. However, these tools are subject to loss and becoming out of adjustment. Each special tool that is required for assembly of the medical device adds to the cost and complexity of the assembly procedure.

Another disadvantage of threaded connections is that the threads may become crossed during initial assembly. If not detected, cross-threading could result in the components not seating properly against each other. Where the attachment is to be fluid tight, poor seating represents a failure that might leak. Tactile feedback is often not available to let the assembler know when the members are properly seated.

Bayonet type connectors have been used to overcome some of the drawbacks of a threaded connectors in medical devices. U.S. Pat. No. 4,737,148 discloses a fluid T coupling comprising a through fluid flow path and an intersecting vent path. The vent path has a filter that is integrally molded with the bayonet connector to be received by an aspirator through path to control the level of vacuum communicated to an irrigation aspiration handpiece during eye surgery.

Patent application DE 2461271 discloses a surgical cannula with a sleeve arranged behind a needle end for connecting to an injection nozzle. The inner space of the sleeve has a connection section for forming a joint of the screw or bayonet type between the sleeve and the injection nozzle.

Patent application CH 632147 discloses a saliva extractor for use in a dental surgery having a suction body and pipe movably coupled together. The two can be arranged to engage together by a bayonet coupling or the pipe can be crimped or expanded at the end. No apparent sealing or resilient locking is apparent.

U.S. Pat. No. 4,494,555 has a surgical instrument for taking skin samples in which a barrel and an end fitting are connected by a bayonet coupling and a spindle and rotor sleeve are connected by a similar second bayonet coupling. This provides for easy disconnection of the barrel and end fitting, thus allowing the fitting and tool to be sterilized separately.

Gasket seals have also been used in connectors for medical devices, and in particular for connections where a fluid tight seal is desired. U.S. Pat. No. 3,076,904 discloses an acoustically vibrated material cutting and removing device which incorporates a gasket seal in a connection between a vibrator element and a tubular retainer. However, the gasket seal is not integral with a bayonet connector.

None of the disclosures above teaches the specific geometry of the present mechanism. In particular, none of the medical instruments disclosed above has a fluid tight bayonet connector which provides the additional features of tactile feedback and over torque protection by means of indexed rotation after seating.

SUMMARY OF THE INVENTION

This invention relates to an improved connector for medical devices where a fluid tight connection is desired between two members. A bayonet style connection is used where the improvements over previous designs include tactile feedback and overtorque protection. A gasket provides a fluid tight seal as well as a restoring force. Overtorquing the connecting members is prevented in this design by the use of an indexed cam pattern that increases the compression of the resilient gasket and the connection when the members are rotated beyond the properly seated position. A connection apparatus for fluid tight attachment of members of a medical device preferably has a first member having a first body and a first connecting end. The first connecting end may have an inner surface. A second member may include a second body and a second connecting end. The second connecting end preferably has an outer surface shaped for telescoping into the inner surface of the first connecting end. A shoulder might be located on the second member. A groove is preferably in the outer surface of the second connecting end. A raised nub of material on the inner surface of the first connecting end could preferably be positioned radially inward to engage the groove. A gasket positioned preferably to bear against the shoulder and be compressed between the first body and the second body. It is preferred that, the gasket be made from an elastomeric material. An engaging trough in the groove may be positioned along the groove to properly hold the first connecting end against the second connecting end. The engaging trough is preferably shaped to stably hold the nub against the groove by the compression force of the gasket. An indexing trough in the groove is preferably positioned along the groove beyond the engaging trough. The indexing trough could be shaped to allow the nub to follow the indexing trough in a manner that will increase compression on the gasket by further increasing the compression between the first connecting end and the shoulder.

The inner surface preferably has more than one raised nub arranged radially and symmetrically about the first connecting end. The outer surface likewise has more than one groove arranged radially and symmetrically about the second connecting end. Each raised nub may be positioned to engage with each groove. The grooves might be connected together such that the indexing trough of each groove will guide the raised nubs to engage the next groove. The inner surface could have more than one raised nub arranged radially and asymmetrically about the first connecting end. The outer surface can have more than one groove arranged radially and asymmetrically about the second connecting end so each raised nub may be positioned to engage with each groove.

A connection apparatus for fluid tight attachment of members of a medical device may have a first member with a first body and a first connecting end. The first connecting end could have an inner surface. A second member might include a second body and a second connecting end so that the second connecting end has an outer surface shaped for telescoping into the inner surface of the first connecting end. A shoulder is located on the second member. A groove is preferably in the inner surface of the first connecting end. A raised nub of material on the outer surface of the second connecting end is preferably positioned radially inward to engage the groove. A gasket positioned to bear against the shoulder may be compressed between the first body and the second body. That gasket might be made from an elastomeric material. An engaging trough in the groove is preferably positioned along the groove to properly hold the first connecting end against the shoulder so the engaging trough is shaped to stably hold the nub against the groove by the compression force of the gasket. An indexing trough in the groove is preferably positioned along the groove beyond the engaging trough. It is desired that, the indexing trough be shaped to allow the nub to follow the indexing trough in a manner that will increase compression on the gasket by further loading the first connecting end against the shoulder.

The outer surface may have more than one raised nub arranged radially and symmetrically about the second connecting end. The inner surface could have more than one groove arranged radially and symmetrically about the first connecting end and each raised nub is then preferably positioned to engage with each groove. The grooves can be connected together such that the indexing trough of each groove will guide the raised nubs to engage the next groove. The outer surface can include more than one raised nub arranged radially and asymmetrically about the second connecting end. The inner surface could desirably have more than one groove arranged radially and asymmetrically about the first connecting end so each raised nub might be positioned to engage with each groove.

A method for fluid tight attachment of members of a medical device may have steps including having a first member with a first connecting end and the first connecting end having an inner surface. Having a second member with a second connecting end perhaps for telescoping the second connecting end into the inner surface of the first connecting end is another step. Locating a groove in the outer surface of the second connecting end for operating the groove as a cam is a further step. Locating a raised nub of material on the inner surface of the first connecting end for positioning the raised nub to engage the groove and for operating the raised nub as a follower for the cam is yet another preferred step. Compressing a gasket seal between the first connecting end and the shoulder while making the gasket seal from an elastomeric material may be a desired step. Positioning an engaging trough in the groove so that the engaging trough is preferably positioned along the groove to properly hold the first connecting end against the second connecting end. The method might include the step of shaping the engaging trough to stably hold the nub against the groove by the compression force of the gasket. Positioning an indexing trough in the groove whereby the indexing trough can be positioned along the groove such that when the nub is rotatably forced past the engaging trough, the nub will follow the indexing trough in a manner that will separate the first connecting end from the second connecting end.

The method also includes the steps of arranging more than one raised nub radially and symmetrically about the first connecting end and arranging more than one groove radially and symmetrically about the second connecting end, and positioning each raised nub to engage with each groove. The method could further include the step of connecting the grooves together such that the indexing trough of each groove will guide the raised nubs to engage the next groove. The method may desirably have the steps of arranging more than one raised nub radially and asymmetrically about the first connecting end and arranging more than one groove radially and asymmetrically about the second connecting end, and positioning each raised nub to engage with each groove.

A method for fluid tight attachment of members of a medical device could have steps including having a first member with a first connecting end wherein the first connecting end having an inner surface. Having a second member with a second connecting end and telescoping the second connecting end into the inner surface of the first connecting end are additional steps. Locating a groove in the inner surface of the first connecting end and the groove operating as a cam are another desired steps. Locating a raised nub of material on the outer surface of the second connecting end and positioning the raised nub to engage the groove while operating the raised nub as a follower for the cam are preferred steps. Compressing a gasket seal between the first connecting end and the shoulder and making the gasket seal from an elastomeric material can be some steps, if preferred, Positioning an engaging trough in and along the groove to properly hold the first connecting end against the shoulder and shaping the engaging trough to stably hold the nub against the groove by the compression force of the gasket are more steps. Positioning an indexing trough in and along the groove such that when the nub is rotatably forced past the engaging trough, the nub will follow the indexing trough in a manner that will retain the first connecting end against the shoulder to a slightly greater degree are steps.

The method might include the steps of arranging more than one raised nub radially and symmetrically about the second connecting end, arranging more than one groove radially and symmetrically about the first connecting end, and positioning each raised nub to engage with each groove. The method can have the step of connecting the grooves together such that the indexing trough of each groove will guide the raised nubs to engage the next groove. The method thereof might have the steps of arranging more than one raised nub radially and asymmetrically about the second connecting end, arranging more than one groove radially and asymmetrically about the first connecting end, and positioning each raised nub to engage with each groove.

DETAILED DESCRIPTION OF THE INVENTION

Figure 1:
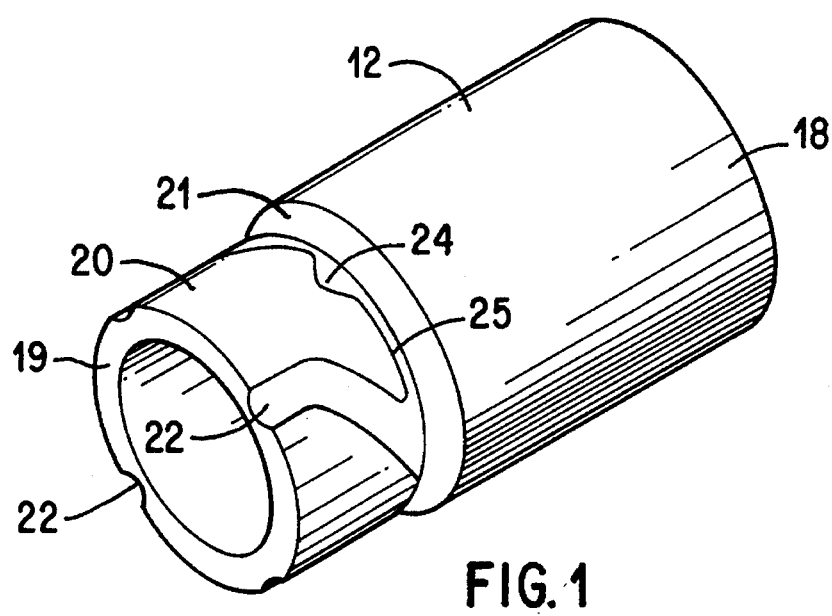
FIG. 1 is a perspective view of one member of a medical device having a connecting end with an outer surface having grooves.
Figure 2:
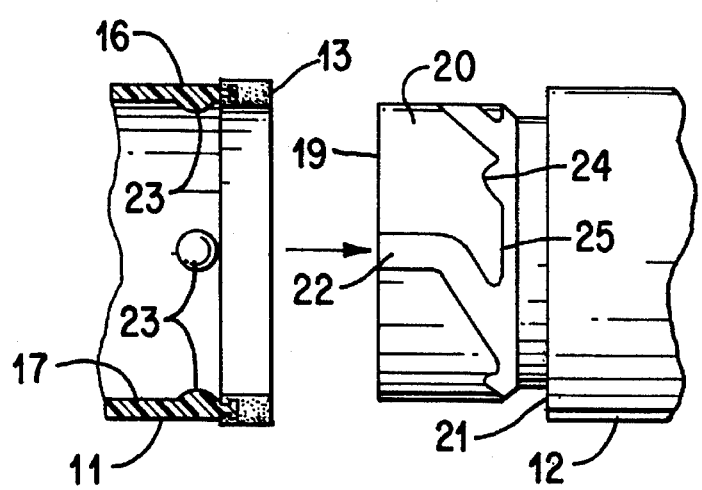
FIG. 2 is a schematic view in partial cross-section of one embodiment of the connection apparatus where both connecting ends are in a separated configuration.
Figure 3:
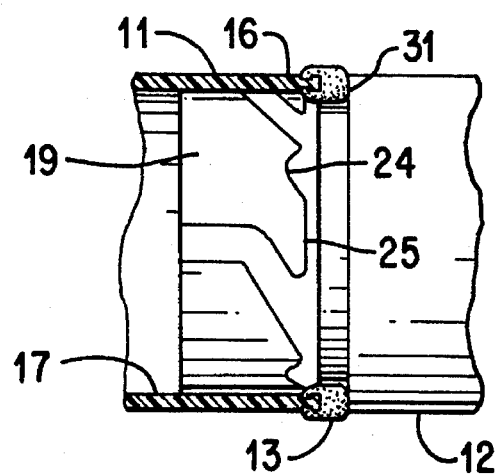
FIG. 3 is a schematic view in partial cross-section of one embodiment of the connection apparatus where both connecting ends are in a connected configuration.
Figure 4:
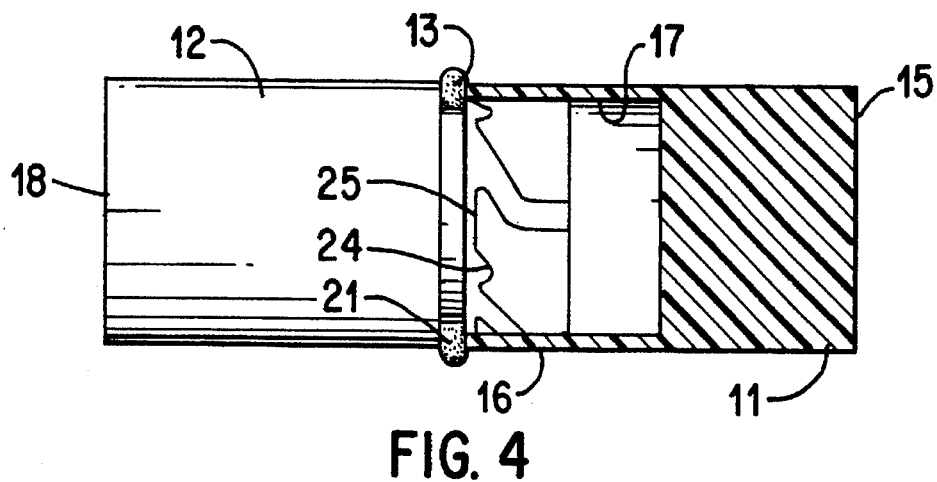
FIG. 4 is a schematic view in partial cross-section of an alternative embodiment of the connection apparatus showing both connecting ends in the connected configuration.
Figure 5:
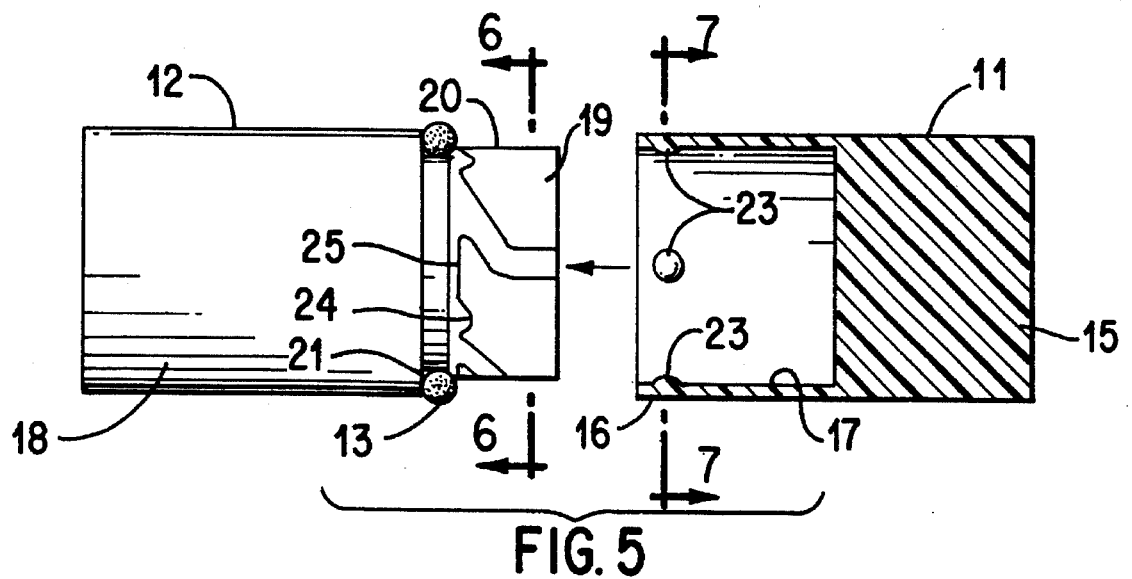
FIG. 5 is a schematic view in partial cross-section of the alternative embodiment of the connection apparatus showing both connecting ends in a separated configuration.

For connecting sections of medical devices with or without the connection being fluid tight a bayonet style joint is used wherein tactile feedback and overtorque protection is provided. The functions of the fluid tight seal and a restoring force are provided by a resilient seal. Overtorquing the connection is prevented with an escape route wherever the sections are rotated beyond their properly seated position. A connection apparatus for fluid tight attachment of first and second members 11 and 12 of any medical device has the first member 11 with its first body 15 and a first connecting end 16. The first connecting end 16 has an inner surface 17. The second member 12 includes a second body 18 and a second connecting end 19 with a distal face. The second connecting end 19 has an outer surface 20 shaped for a telescoping fit into and within the inner surface 17 of the first connecting end 16. A shoulder 21 located on the second member 12 in FIG. 5 at the junction between the corresponding first body 15 or second body 18 and the corresponding first connecting end 16 and the shoulder 21 is provided. A groove 22 is in the outer surface 20 of the second connecting end 19. A raised nub 23 of material on the inner surface 17 of the first connecting end 16 is positioned to extend from the inner surface 17 radially inward to engage the groove 22. A gasket 13 positioned to bear against the shoulder 21 and be compressed between the first body 15 and the second body 18 as the fluid tight seal. The gasket 13 is made from an elastomeric material, preferably silicone having a low durometer of about 55 A. An engaging trough 24 in the groove 22 is positioned along the groove 22 to properly hold the first connecting end 16 against the shoulder 21. The engaging trough 24 is shaped to stably hold the nub 23 against the groove 22 due to the force supplied by the compressed gasket 13.

An indexing trough 25 in the groove 22 is positioned along the groove 22 beyond the engaging trough 24. The indexing trough 25 is shaped to allow the nub 23 to follow the indexing trough 25 in a manner that will retain the compression on the gasket 13 by at least slightly compressing the first connecting end 16 against shoulder 21 at a degree which the user can recognize. Most importantly, the slight additional compression does not over stress either first connecting body 15 or the second connecting body 18.

Figure 6:
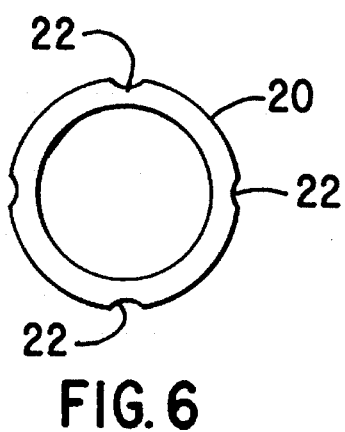
FIG. 6 is a partial cross-section of a connecting end taken through the axis 6—6.
Figure 7:
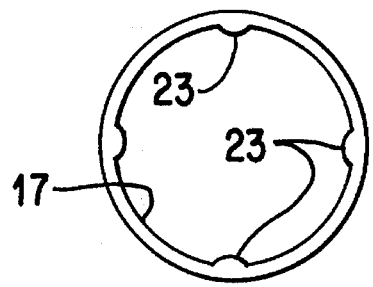
FIG. 7 is a partial cross-section of a connecting end taken through the axis 7—7.

In one alternative embodiment shown in FIG. 7, the inner surface 17 has more than one raised nub 23 so that each is arranged to extend radially from the inner surface 17 and symmetrically about the first connecting end 16. The outer surface 20 likewise has more than one groove 22, see FIG. 6 arranged radially and symmetrically about the second connecting end 19. Each raised nub 23 is thus positioned to engage with each groove 22. The grooves 22 are connected together such that the indexing trough 25 of each groove 22 will guide the raised nubs 23 extending thereinto for engagement with the next groove 22 thereafter when the members 11 and 12 are rotated relative to one another.

If the positions of the respective nubs 23 and grooves 22 are not symmetrical then a one position connection for the members 11 and 12 is provided. The inner surface 17 in one embodiment has more than one raised nub 23 extending therefrom and positioned radially and asymmetrically there on and about the first connecting end 16; the outer surface 20 for mating therewith has more than one groove 22 arranged radially and asymmetrically therein and about the second connecting end 19. Each raised nub 23 is thus positioned to engage with its respective groove 22 when the members 11 and 12 are assembled for fluid tight connection.

Figure 9:
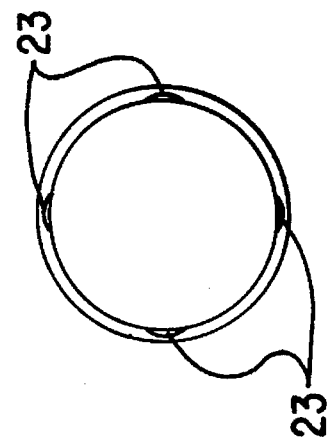
FIG. 9 is a partial cross-section of a connecting end taken through the axis 9—9 of FIG. 8.
Figure 8:
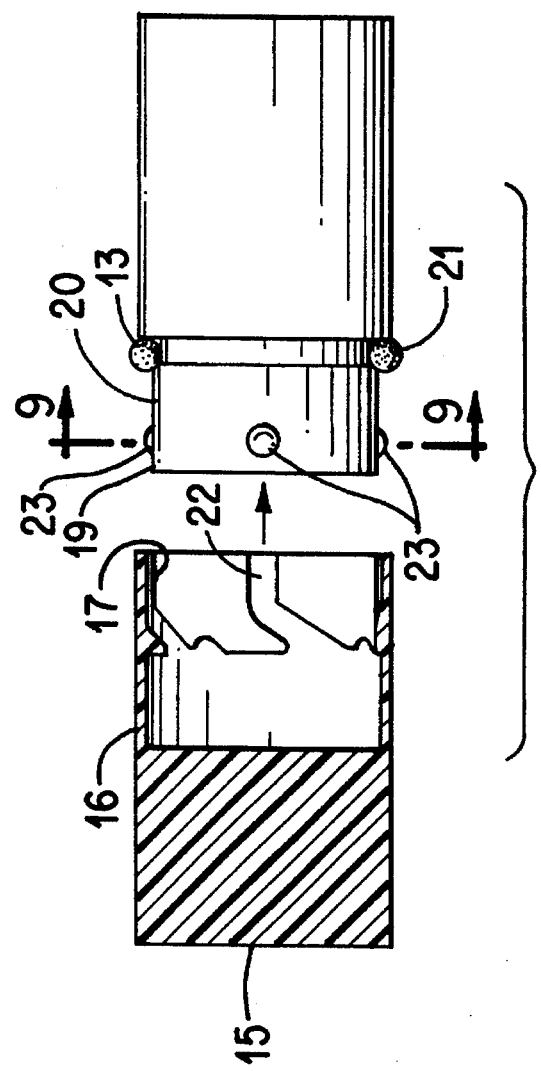
FIG. 8 is a schematic view in partial cross-section of another alternative embodiment of the connection apparatus showing both connecting ends in a separated configuration.

As an alternate, as shown in FIGS. 8 and 9, the relationship between the groove 22 and the nub 23 can be reversed. Thus, the groove 22 would be located in the inner surface 17 of the first connecting end 16. The raised nub 23 of material would be on the outer surface 20 of the second connecting end 19 positioned to extend radially outward to engage the groove 22. The gasket 13 remains positioned to bear against the shoulder 21 and is compressed between the first body 15 and the shoulder 21.

The engaging trough 24 in the groove 22 is positioned along the groove 22 to properly hold the first connecting end 16 assembled to the second connecting end 19 because the engaging trough 24 has a shape to stably hold the nub 23 against the groove 22 by the compression force of the gasket 13. The indexing trough 25 of inner surface 17 in this embodiment is part of groove 22 and is positioned along the groove 22 beyond the engaging trough 24. The indexing trough 25 is shaped to allow the nub 23 to follow the indexing trough 25 so as to retain the compression on the gasket 13 by at least slightly increasing the loading so that the rotation past the engaging trough is readily apparent and the first connecting end 16 is against the shoulder 21.

Similarly, the outer surface 20 of the connection apparatus can have more than one raised nub 23 extending therefrom and arranged radially and symmetrically about the second connecting end 19. The inner surface 17 would then have more than one groove 22 position therein and arranged radially and symmetrically about the first connecting end 16 and each raised nub 23 is positioned to permit engagement with each groove. The grooves can be continued to be connected together such that the indexing trough 25 of each groove 22 guides the conjugating raised nubs to engage the next part of the groove 22. If the outer surface 20 includes more than one raised nub 23 extending therefrom and arranged radially and asymmetrically about the second connecting end 19, the inner surface 17 would have more than one groove 22 therein arranged radially and asymmetrically about the first connecting end 16 so each raised nub 23 is positioned to engage with a respective groove 22.

A method for fluid tight attachment of members 11 and 12 of a medical device has steps including having a first member 11 with a first connecting end 16 and the first connecting end 16 having its inner surface 17. Having second member 12 with second connecting end 19 for a telescoping fit between the second connecting end 19 into the inner surface 17 of the first connecting end 16 is another step. Locating groove 22 in the outer surface 20 of the second connecting end 19 for operating the groove 22 as cam 14 is a further step. Locating nub 23 of material on the inner surface 17 of the first connecting end 16 for positioning the raised nub 23 to engage the groove 22 and for operating the raised nub 23 as a follower for the cam 14 is yet another step when the connecting ends 16 and 19 are brought together as an assembly. Compressing gasket 13 to seal between the first connecting end 16 and the shoulder 21 while making the gasket 13 seal as a resilient elastomeric material is a step then performed. Positioning engaging trough 24 in the groove 22 so that the engaging trough 24 is located along the groove 22 to properly hold the first connecting end 16 against the shoulder 21. The method has the step of shaping the engaging trough 24 to stably hold the nub 23 against the groove 22 by the compression force of the gasket 13. Positioning indexing trough 25 in the groove 22 whereby the indexing trough 25 can be located along the groove 22 such that when the nub 23 is rotatably forced past the engaging trough, the nub 23 will follow the indexing trough 25 in a manner that will further compress the first connecting end 16 against the shoulder 21.

The method also includes the steps of arranging more than one raised nub 23 radially and symmetrically about the first connecting end 16 and arranging more than one groove 22 radially and symmetrically about the second connecting end 19, and positioning each raised nub 23 to engage with a respective groove 22. The method could further include the step of connecting the grooves 22 together such that the indexing trough 25 of each groove 22 will guide the raised nubs 23 to engage the next groove. The method has the steps of arranging more than one raised nub 23 radially and asymmetrically about the first connecting end 16 and arranging more than one groove 22 radially and asymmetrically about the second connecting end 19, and positioning each raised nub 23 to engage with its respective groove 22.

A method for fluid tight attachment of members 11 and 12 of a medical device could have steps including having first member 11 with its first connecting end 16 wherein the first connecting end 16 has inner surface 17. Having second member 12 with its second connecting end 19 and the step of telescoping the second connecting end 19 into the inner surface 17 of the first connecting end 16. Locating groove 22 in the inner surface 17 of the first connecting end 16 and the groove 22 operating as cam 14 are other steps. Locating raised nub 23 of material on the outer surface 20 of the second connecting end 19 and positioning the raised nub 23 to engage the groove 22 while operating the raised nub 23 as a follower for the cam 14 are more steps. Compressing gasket 13 to seal between the first connecting end 16 and the shoulder 21 arid making the gasket 13 as a seal from an elastomeric material are added steps. Positioning engaging trough 24 in and along the groove 22 to properly hold the first connecting end 16 against the shoulder 21 and shaping the engaging trough 24 to stably hold the nub 23 against the groove 22 by the compression force of the gasket 13 are more steps. Positioning indexing trough 25 in and along the groove 22 such that when the nub 23 is rotatably forced past the engaging trough 24 so the nub 23 will follow the indexing trough 25 in a manner that will indicate to the user that the nub 23 is no longer in the engaging trough when the first connecting end 16 bears against the shoulder 21 to a slightly greater degree is a step.

The method includes the steps of arranging more than one raised nub 23 radially and symmetrically about the second connecting end 19, arranging more than one groove 22 radially and symmetrically about the first connecting end 16, and positioning each raised nub 23 to engage with each groove 22. The method has the step of connecting the grooves 22 together such that the indexing trough 25 of each groove 22 will guide the raised nubs 23 therein to engage the next groove 22. The method thereof has the steps of arranging more than one raised nub 23 radially and asymmetrically about the second connecting end 19, arranging more than one groove 22 radially and asymmetrically about the first connecting end 16, and positioning each raised nub 23 to engage with its respective groove 22.

While a particular configuration has been shown the concept and technique is in its broadest context is the tight interengagement of members 11 and 12 through a connection including compressible gasket 13 as a holding device to keep the nub 23 in the engaging trough 24. A further feature is the ability to not overtorque the connection of the members 11 and 12. The claims hereof which follow seek to protect the expansive or broadest execution of the concept and technique.

What is claimed is:

1. A connection apparatus for fluid tight attachment of members of a medical device, the apparatus comprising:

a first member having a first body and a first connecting end, the first connecting end having an inner surface;

a second member having a second body and a second connecting end, the second connecting end having a distal face and an outer surface shaped for telescoping into the inner surface of the first connecting end;

a shoulder located on the second members a groove in the outer surface of the second connecting end extending from the distal face thereof to said shoulder;

a raised nub of material on the inner surface of the first connecting end, the raised nub positioned radially inward to engage the groove;

a gasket, the gasket positioned to bear against the shoulder, the gasket to be compressed between the first body and the second body, the gasket made from an elastomeric material;

an engaging trough in the groove, the engaging trough positioned along the groove to properly hold the first connecting end against the second connecting end thereby compressing said gasket, the engaging trough shaped to stably hold the nub against the engaging trough by the compression force of the gasket;

an indexing trough in the groove, the indexing trough positioned along the groove beyond the engaging trough, the indexing trough shaped to allow the nub to follow the indexing trough in a manner that will increase compression on the gasket by further loading the first connecting end towards the shoulder; and the indexing trough further shaped to extend about the outer surface in a manner that will prevent over torquing the connection apparatus when the nub is forced past the engaging trough and moved within the groove while the first connecting end and the second connecting end are in telescopic relationship.

2. The apparatus of claim 1 wherein the inner surface has more than one raised nub arranged radially and symmetrically about the first connecting end, the outer surface has more than one groove arranged radially and symmetrically about the second connecting end, and each raised nub is positioned to engage with each groove.

3. The apparatus of claim 2 wherein the grooves are connected together such that the indexing trough of each groove will guide the raised nubs to engage the next groove.

4. The apparatus of claim 1 wherein the inner surface has more than one raised nub arranged radially and asymmetrically about the first connecting end, the outer surface has more than one groove arranged radially and asymmetrically about the second connecting end, and each raised nub is positioned to engage with each groove.

5. A connection apparatus for fluid tight attachment of members of a medical device, the apparatus comprising:

a first member having a first body and a first connecting end, the first connecting end having an inner surface and a distal face;

a second member having a second body and a second connecting end, the second connecting end having an outer surface shaped for telescoping into the inner surface of the first connecting end;

a shoulder located on the second member;

a groove in the inner surface of the first connecting end extending from the distal face thereof toward said first body;

a raised nub of material on the outer surface of the second connecting end, the raised nub positioned radially inward to engage the groove;

a gasket, the gasket positioned to bear against the shoulder, the gasket to be compressed between the first body and the second body, the gasket made from an elastomeric material;

an engaging trough in the groove, the engaging trough positioned along the groove to properly hold the first connecting end against the second connecting end thereby compressing said gasket, the engaging trough shaped to stably hold the nub against the engaging trough by the compression force of the gaskets;

an indexing trough in the groove, the indexing trough positioned along the groove beyond the engaging trough, the indexing trough shaped to allow the nub to follow the indexing trough in a manner that will increase compression on the gasket by further loading the first connecting end towards the shoulder, and the indexing trough further shaped to extend about the inner surface in a manner that will prevent over torquing the connection apparatus when the nub is forced past the engaging trough and groove while the first connecting end and the second connecting end are in telescopic relationship.

6. The apparatus of claim 5 wherein the outer surface has more than one raised nub arranged radially and symmetrically about the second connecting end, the inner surface has more than one groove arranged radially and symmetrically about the first connecting end, and each raised nub is positioned to engage with each groove.

7. The apparatus of claim 6 wherein the grooves are connected together such that the indexing trough of each groove will guide the raised nubs to engage the next groove.

8. The apparatus of claim 5 wherein the outer surface has more than one raised nub arranged radially and asymmetrically about the second connecting end, the inner surface has more than one groove arranged radially and asymmetrically about the first connecting end, and each raised nub is positioned to engage with each groove.

9. A method for fluid tight attachment of members of a medical device, the method including the steps of:

having a first member with a first connecting end, the first connecting end having an inner surface;

having a second member with a second connecting end, the second connecting end having a distal face, telescoping the second connecting end into the inner surface of the first connecting end;

locating a groove in the outer surface of the second connecting end extending from the distal face thereof to said shoulder, operating the groove as a cam;

locating a raised nub of material on the inner surface of the first connecting end, positioning the raised nub to engage the groove, operating the raised nub as a follower for the cam;

compressing a gasket seal between the first connecting end and the shoulder, making the gasket seal from an elastomeric material;

positioning an engaging trough in the groove, the engaging trough positioned along the groove to properly hold the first connecting end against the second connecting end thereby compressing said gasket, shaping the engaging trough to stably hold the nub against the engaging trough by the compression force of the gasket;

positioning an indexing trough in the groove, the indexing trough positioned along the groove;

preventing over torquing when the nub is rotatably forced past the engaging trough, and following the indexing trough with the nub in a manner that will prevent over torquing the connection apparatus.

10. The method of claim 9 including the steps of arranging more than one raised nub radially and symmetrically about the first connecting end, arranging more than one groove radially and symmetrically about the second connecting end, and positioning each raised nub to engage with each groove.

11. The method of claim 10 including the step of connecting the grooves together such that the indexing trough of each groove will guide the raised nubs to engage the next groove.

12. The method of claim 9 including the steps of arranging more than one raised nub radially and asymmetrically about the first connecting end, arranging more than one groove radially and asymmetrically about the second connecting end, and positioning each raised nub to engage with each groove.

13. A method for fluid tight attachment of members of a medical device, the method including the steps of:

having a first member with a first body and a first connecting end, the first connecting end having an inner surface and a distal face;

having a second member with a second connecting end, telescoping the second connecting end into the inner surface of the first connecting end;

locating a groove in the inner surface of the first connecting end extending from the distal face thereof toward said first body, the groove operating as a cam;

locating a raised nub of material on the outer surface of the second connecting end, positioning the raised nub to engage the groove, operating the raised nub as a follower for the cam;

compressing a gasket seal between the first connecting end and the shoulder, making the gasket seal from an elastomeric material;

positioning an engaging trough in the groove, the engaging trough positioned along the groove to properly hold the first connecting end against the gasket thereby compressing said gasket, shaping the engaging trough to stably hold the nub against the engaging trough by the compression force of the gasket;

positioning an indexing trough in the groove, the indexing trough positioned along the groove;

preventing over torquing when the nub is rotatably forced past the engaging trough, and following the indexing trough with the nub in a manner that will prevent over torquing the connection apparatus.

14. The method of claim 13 including the steps of arranging more than one raised nub radially and symmetrically about the second connecting end, arranging more than one groove radially and symmetrically about the first connecting end, and positioning each raised nub to engage with each groove.

15. The method of claim 14 including the step of connecting the grooves together such that the indexing trough of each groove will guide the raised nubs to engage the next groove.

16. The method of claim 13 including the steps of arranging more than one raised nub radially and asymmetrically about the second connecting end, arranging more than one groove radially and asymmetrically about the first connecting end, and positioning each raised nub to engage with each groove.

* * * * *